(12) United States Patent
Ma et al.

(10) Patent No.: US 8,063,257 B2
(45) Date of Patent: Nov. 22, 2011

(54) METHOD FOR PRODUCING 2,3,3,3-TETRAFLUOROPROPENE

(75) Inventors: Jing Ji Ma, Skokie, IL (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 727 days.

(21) Appl. No.: 12/192,519

(22) Filed: Aug. 15, 2008

(65) Prior Publication Data

US 2009/0030245 A1 Jan. 29, 2009

Related U.S. Application Data

(63) Continuation-in-part of application No. 11/619,592, filed on Jan. 3, 2007.

(51) Int. Cl.
*C07C 21/18* (2006.01)
(52) U.S. Cl. .................................................. 570/136
(58) Field of Classification Search .................. None
See application file for complete search history.

(56) References Cited

U.S. PATENT DOCUMENTS

| 2,931,840 A | 4/1960 | Marquis et al. |
| 2,996,555 A | 5/1961 | Rausch |
| 5,162,594 A | 11/1992 | Krespan |
| 6,031,141 A * | 2/2000 | Mallikarjuna et al. ........ 570/136 |
| 2007/0197841 A1 | 8/2007 | Mukhopadhyay et al. |

FOREIGN PATENT DOCUMENTS

| EP | 0328148 A1 | 8/1989 |
| JP | 63211245 A | 9/1988 |

OTHER PUBLICATIONS

A Henne, et al; "Fluorinated Derivatives of Propane and Propylene"; Journal of the American Chemical Society, American Chemical Society, New York, USA; vol. 68, Jan. 1, 1946; pp. 496-497; XP002322185.
Banks et al., Preparation of 2,3,3,3-Tetrafluoropropene From Trifluoroacetylacetone and Sulphur Tetrafluoride, Journal of Fluorine Chemistry, 1997, 171-174, 82, Manchester, UK.
Mcbee et al., Highly Halogenated Alkanes Derived From Fluorine-Containing Alcohols, Journal of American Chemical Society, 1953, 3149, 77, USA.
Zhurnal Organicheskoi Khimii (1971), 7 (9), 1181.
Journal of Organic Chemistry (CA 99:21908) USSR.

* cited by examiner

*Primary Examiner* — Daniel M Sullivan
*Assistant Examiner* — Yevegeny Valenrod
(74) *Attorney, Agent, or Firm* — Bruce Bradford

(57) ABSTRACT

A method for preparing 2,3,3,3-tetrafluoropropene comprising contacting a reactant comprising $CCl_2\!=\!CFCH_2Cl$ with a fluorinating agent, such as HF, under conditions effective to produce a reaction product comprising $CF_3CF\!=\!CH_2$.

16 Claims, No Drawings

METHOD FOR PRODUCING 2,3,3,3-TETRAFLUOROPROPENE

CROSS-REFERENCES TO RELATED APPLICATIONS

This application is a continuation-in-part of U.S. patent application Ser. No. 11/619,592, filed Jan. 3, 2007, the disclosure of which is incorporated herein by reference.

BACKGROUND OF INVENTION (1) Field of Invention

This invention relates to novel methods for preparing fluorinated organic compounds, and more particularly to methods of producing fluorinated olefins.

(2) Description of Related Art

Hydrofluorocarbons (HFCs), including particular hydrofluoroalkanes such as tetrafluoropropenes (e.g., 2,3,3,3-tetrafluoro-1-propene (HFO-1234yf)) are effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFO-1234yf does not contain chlorine and, thus, poses no threat to the ozone layer. Also, HFO-1234yf possesses a relatively low Global Warming Potential (GWP) compared to most CFCs and HCFCs.

Methods of synthesizing certain HFOs are known. For example, preparation of HFO-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product. These starting materials can be expensive, difficult to handle, and/or result in low yields. However, $CCl_2$=$CClCH_2Cl$ can be used as an inexpensive and readily available starting material for the preparation of $CH_2$=$CFCF_3$ using the following three-step process:

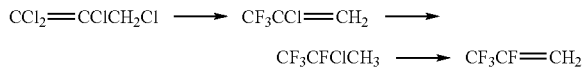

However, such multistep processes are generally more complicated and less economical compared to shorter synthesis routes. Accordingly, there remains a need for a direct route to convert readily available and inexpensive starting materials. Such starting materials for the synthesis of HFO-1234yf have heretofore been unknown.

SUMMARY OF INVENTION

Applicants have found a novel method for synthesizing HFO-1234yf that involves fluorinating $CCl_2$=$CFCH_2Cl$. In this invention, the fluorine atom on center carbon of $CF_3CF$=$CH_2$ is introduced in the preparation of $CCl_2$=$CFCH_2Cl$ (for example, by the addition of HF to $CH_2$=$CClCH_2Cl$ or to $CHCl$=$CClCH_2Cl$ or by the chlorofluorination of $CH_2$=$CClCH_2Cl$). This makes the total process shorter than the prior art process. Although $CCl_2$=$CFCH_2Cl$ is a known compound, its advantageous use as a reactant in the synthesis of HFO-1234yf was unknown despite the desirability of such reactant.

Accordingly, in a certain aspect of the invention provided is a method for preparing 2,3,3,3-tetrafluoropropene comprising contacting a reactant comprising $CCl_2$=$CFCH_2Cl$ with a fluorinating agent under conditions effective to produce a reaction product comprising $CF_3CF$=$CH_2$.

According to another aspect of the invention, provided is a method for preparing 2,3,3,3-tetrafluoropropene comprising: providing a precursor composition comprising at least one tetrachlorofluoropropane; dehydrochlorinating at least one tetrachlorofluoropropane to produce a first amount of at least one trichlorofluoropropene selected from the group consisting of $CCl_2$=$CFCH_2Cl$ and $CH_2$=$CFCCl_3$; optionally, contacting said $CH_2$=$CFCCl_3$ with an isomerization catalyst to produce a second amount of $CCl_2$=$CFCH_2Cl$; and contacting a reactant comprising said first amount of said trichlorofluoropropene and, optionally, said second amount of $CCl_2$=$CFCH_2Cl$ with a fluorinating agent under conditions effective to produce a reaction product comprising $CF_3CF$=$CH_2$.

DETAILED DESCRIPTION OF PREFERRED EMBODIMENTS OF THE INVENTION

In general, the catalytic fluorination of $CCl_2$=$CFCH_2Cl$ with HF to produce $CF_3CF$=$CH_2$ can be conducted in the liquid phase, in the gas phase or in a combination of gas and liquid phases, and it is contemplated that the reaction can be carried out batch wise, continuous, or a combination of these.

As used herein, the term "directly converting" means converting in a single reaction or under essentially one set of reaction conditions.

For embodiments in which the reaction comprises a liquid phase reaction, the reaction can be catalytic or non-catalytic. Preferably, a catalytic process is used. Lewis acid catalysts, such as metal-halide catalysts, including antimony halides, tin halides, thallium halides, iron halides, and combinations of two or more of these, are preferred in certain embodiments. Metal chlorides and metal fluorides are particularly preferred. Examples of particularly preferred catalysts of this type include $SbCl_5$, $SbCl_3$, $SbF_5$, $SbCl_nF_{5-n}$ wherein n is an integer from 1 to 4, $SnCl_4$, $TiCl_4$, $FeCl_3$, and combinations of two or more of these.

For embodiments in which the reaction comprises a vapor phase reaction, the reaction preferably is at least partially catalyzed, and is preferably carried out on a continuous basis by introducing the reactant and fluorinating agent as one or more streams into one or more reaction vessels. In certain embodiments, the gas phase reaction is conducted in a continuous manner by introducing a stream of $CCl_2$=$CFCH_2Cl$ (preferably preheated to a temperature of about 150° C.), into a reaction vessel where it is contacted with catalyst and HF at a temperature of about 200-500° C. (preferably about 250-450° C., and more preferably about 300-400° C.). The mole ratio of HF to $CCl_2$=$CFCH_2Cl$ can range from about 3 to 1 (stoichiometric amount) to about 20 to 1. The preferred catalysts are chromium-based catalysts (such as $Cr_2O_3$ including fluorinated chromium oxide) and iron-based catalysts (such as $FeCl_3$) or combinations of these. Other catalysts are activated carbon and activated carbon containing transition metal salts (e.g. Co, Fe, Cu, and Mn) and transition metal salts on inert support materials (e.g. aluminum fluoride).

Preferred contact times are those that achieve good conversion and will vary depending on the activity of the catalyst. In certain embodiments, contact times are selected for good productivity and will generally range from about 1 to about 60 seconds, more preferably from about 1 to about 10 seconds, and still more preferably about 2 to about 5 seconds.

The reaction vessels for liquid and gas phase reactions are comprised of materials which are resistant to corrosion by HF and HCl, such as Hastelloy, Inconel, and Monel.

The reaction pressure can be varied over a considerable range in order to adjust contact times so as to achieve desired levels of conversion and yield.

The present invention is preferably carried out under conditions, including the use of one or more reactions, effective to produce a reaction product having a HFO-1234yf yield of at least about 50%, more preferably at least about 75%, and even more preferably at least about 90%. In certain preferred embodiments the conversion is at least about 95%, and more preferably at least about 97%.

The compound $CH_3CFClCCl_3$ can be converted into $CH_2=CFCCl_3$ via dehydrochlorination and subsequently isomerized to the desired $CCl_2=CFCH_2Cl$. The dehydrochlorination of $CH_3CFClCCl_3$ can be a liquid or vapor phase catalytic reaction. Depending on the dehydrochlorination conditions, two isomeric products, $CH_2=CFCCl_3$ and $CCl_2=CFCH_2Cl$, can be formed from $CH_3CFClCCl_3$. The dehydrochlorination of $CH_3CFClCCl_3$ with NaOH at lower temperatures leads to $CH_2=CFCCl_3$, but from liquid and vapor phase catalytic reactions (using activated carbon or $FeCl_3$ catalysts, for example), the product is $CCl_2=CFCH_2Cl$. Thus, under certain conditions, the dehydrochlorination and isomerization can take place in one reaction step.

Alternatively, $CCl_2=CFCH_2Cl$ can be prepared by the dehydrochlorination of $CHCl_2CFClCH_2Cl$ which in turn can be made by the chlorination of $CH_2ClCFClCH_2Cl$ (see, e.g., Zhurnal Organicheskoi Khimii (1971), 7(9), 1181).

EXAMPLES

Example 1

$CF_3CF=CH_2$ by Vapor Phase Fluorination of $CCl_2=CFCH_2Cl$

Ten cubic centimeters of pre-dried, fluorinated $Cr_2O_3$ catalyst is placed in a 50 cm long Monel tube of 10 mm diameter, which is heated in tube furnace. The inlet side of the tube is connected to an HF cylinder and a syringe pump with $CCl_2=CFCH_2Cl$. The outlet side of the tube is connected to a trap cooled in dry ice-acetone followed by an acid scrubber. During the reaction, the temperature is controlled at 350° C., while the HF addition is controlled at 5 g (0.25 mole) per hour and the rate of $CCl_2=CFCH_2Cl$ addition is 10 g (0.06 mole) per hour for a contact time of 2.3 seconds. After the reaction, the crude product in the cold trap is slowly warmed up, and the product, along with HF is bubbled into water and then into another cold trap to condense the product, $CF_3CF=CH_2$.

Example 2

Isomerization of $CH_2=CFCCl_3$ to $CCl_2=CFCH_2Cl$

Fifty grams of $CH_2=CFCCl_3$ and 5 g of 4.6% $FeCl_3/C$ catalyst is stirred in a flask at 100° C. After the reaction is complete, as determined by GC analysis, the catalyst is filtered out and the $CCl_2=CFCH_2Cl$ used directly for fluorination.

Example 3

Dehydrochlorination of $CH_3CFClCCl_3$ with NaOH to Give $CH_2=CFCCl_3$

A 250 mL three necked flask is equipped with stir bar, solid additional funnel, distillation head, condenser and receiver. $CH_3CFClCCl_3$ (72 g, 0.36 mole) is placed in the flask, and crushed solid NaOH (15 g, 0.36 mole) is placed in the funnel. The $CH_3CFClCCl_3$ is heated in to about 150-175° C. with an oil bath. Solid NaOH is then added over about one hour with stirring. During the reaction, $CCl_3CF=CH_2$ distills out as it is formed.

Example 4

Liquid Phase Catalytic Dehydrochlorination of $CH_3CFClCCl_3$ to Give $CCl_2=CFCH_2Cl$ Five grams of anhydrous $FeCl_3$ and 100 g $CH_3CFClCCl_3$ are charged in a 250 mL flask, which is equipped with reflux condenser and stir bar. The top of the reflux is connected to an acid scrubber. The flask is heated in oil bath with stirring until $CH_3CFClCCl_3$ has melted and then the mixture is maintained at this temperature (130-140° C.) for 10 h. The product is distilled to collect $CCl_2=CFCH_2Cl$, bp 129° C.

Example 5

Vapor Phase Catalytic Dehydrochlorination of $CH_3CFClCCl_3$ to Give $CCl_2=CFCH_2Cl$ Ten grams of 4.6% $FeCl_3/C$ catalyst is placed in a Monel tube of 10 mm diameter, which is heated in a tube furnace. The inlet side of the tube is connected to a flow meter and $N_2$ source, and to a source of $CH_3CFClCCl_3$. The outlet side of the tube is connected to a product receiver, which is cooled in dry ice and connected to an HCl scrubber. During the reaction the tube is heated to 200° C. Nitrogen flow rate is maintained at 10 cc/minute while the addition rate of $CH_3CFClCCl_3$ is 0.2 g/min. The crude dehydrochlorination product in the cold trap is distilled to give pure $CCl_2=CFCH_2Cl$.

Example 6

Dehydrochlorination of $CHCl_2CFClCH_2Cl$ to Give $CHCl=CClCH_2Cl$

The same procedure as in Example 5 is used.

Example 7

Chlorination of $CH_2ClCFClCH_2Cl$ for $CHCl_2CFClCH_2Cl$

A 250 mL three neck flask is equipped with stir bar, thermometer, and a reflux condenser maintained at −5° C. A provision is made to introduce chlorine into the flask from a chlorine cylinder, the $Cl_2$ flow being controlled with flow meter. The top of the condenser is connected to HCl and $Cl_2$ scrubbers. $CH_2ClCFClCH_2Cl$ (126 g or 0.76 mole) is placed in the flask which is then heated in an oil bath at 140-150° C. $Cl_2$ is bubbled subsurface into the $CH_2ClCFClCH_2Cl$ at 10 g per hour. After adding 54 g (0.76 mole) of $Cl_2$ the reaction mixture is fractionated to separate $CHCl_2CFClCH_2Cl$.

Example 8

Liquid Phase HF Addition to $CHCl=CClCH_2Cl$ to Give $CHCl_2CFClCH_2Cl$

Two moles (270 g) of $CHCl=CClCH_2Cl$ and 2.2 g (0.008 mole) of $TaF_5$ are charged to a 500 mL autoclave. The reactor is closed and evacuated in dry-ice acetone. 40 g (2 mole) anhydrous HF is added. The reaction mixture is stirred at room temperature for 24 hours. The crude product mixture is carefully poured onto crushed ice, and the organic layer is separated, washed with water and dried.

Having thus described a few particular embodiments of the invention, it will be apparent to those skilled in the art, in view of the teachings contained herein, that various alterations, modifications, and improvements not specifically described are available and within the scope of the present invention. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for preparing 2,3,3,3-tetrafluoropropene comprising contacting a reactant comprising $CCl_2=CFCH_2Cl$ with a fluorinating agent under conditions effective to produce a reaction product comprising $CF_3CF=CH_2$, wherein contacting the said reactant is performed in the presence of at least one catalyst selected from the group consisting of chromium(III)oxide, fluorinated chromium oxide, iron(III) chloride, activated carbon, transition metal halides, $SbCl_5$, $SbCl_nF_{5-n}$, $SnCl_4$, $TiCl_4$, and $FeCl_3$, wherein n is an integer from 0 to 4.

2. The method of claim 1 wherein said contacting directly converts said reactant into said reaction product.

3. The method of claim 1 wherein said fluorinating agent is HF.

4. The method of claim 1 wherein said contacting involves a gas phase reaction.

5. The method of claim 4 wherein said gas phase reaction involves at least one catalyst selected from the group consisting of chromium(III) oxide, fluorinated chromium oxide, iron (III) chloride, activated carbon, and transition metal halides.

6. The method of claim 5 wherein said HF and said $CCl_2=CFCH_2Cl$ are present in a molar ratio of about 3:1 to about 20:1 during at least a portion of said gas phase reaction.

7. The method of claim 1 wherein said contacting involves a liquid phase reaction.

8. The method of claim 7 wherein said liquid phase reaction involves at least one catalyst selected from the group consisting of $SbCl_5$, $SbCl_nF_{5-n}$, $SnCl_4$, $TiCl_4$, and $FeCl_3$, wherein n is an integer from 0 to 4.

9. The method of claim 1 further comprising:
providing a precursor composition comprising $CH_2=CFCCl_3$; and
contacting said precursor composition with an isomerization catalyst to produce said $CCl_2=CFCH_2Cl$.

10. The method of claim 9 wherein said isomerization catalyst comprises an iron(III) chloride/carbon catalyst.

11. A method for preparing 2,3,3,3-tetrafluoropropene comprising:
providing a precursor composition comprising at least one tetrachlorofluoropropane;
dehydrochlorinating at least one tetrachlorofluoropropane to produce a first amount of at least one trichlorofluoropropene selected from the group consisting of $CCl_2=CFCH_2Cl$ and $CH_2=CFCCl_3$;
optionally, contacting said $CH_2=CFCCl_3$ with an isomerization catalyst to produce a second amount of $CCl_2=CFCH_2Cl$; and
contacting a reactant comprising said first amount of first amount of said $CCl_2=CFCH_2Cl$ and, optionally, said second amount of $CCl_2=CFCH_2Cl$ with a fluorinating agent under conditions effective to produce a reaction product comprising $CF_3CF=CH_2$, wherein contacting the said reactant is performed in the presence of at least one catalyst selected from the group consisting of chromium(III)oxide, fluorinated chromium oxide, iron(III) chloride, activated carbon, transition metal halides, $SbCl_5$, $SbCl_nF_{5-n}$, $SnCl_4$, $TiCl_4$, and $FeCl_3$, wherein n is an integer from 0 to 4.

12. The method of claim 11 wherein said tetrachlorofluoropropane is selected from the group consisting of $CH_3CFClCCl_3$, $CHCl_2CFClCH_2Cl$, or combination of these.

13. The method of claim 12 wherein said isomerization catalyst comprises an iron(III) chloride/carbon catalyst.

14. The method of claim 12 wherein said dehydrochlorinating involves contacting said tetrachlorofluoropropane with NaOH.

15. The method of claim 12 wherein said dehydrochlorinating involves a liquid phase catalytic reaction.

16. The method of claim 12 wherein said dehydrochlorinating involves a vapor phase catalytic reaction.

* * * * *